US010899681B2

(12) United States Patent
Lefort et al.

(10) Patent No.: US 10,899,681 B2
(45) Date of Patent: *Jan. 26, 2021

(54) PROCESS FOR THE PREPARATION OF DEUTERATED ETHANOL FROM D2

(71) Applicant: Deuteria Beverages, LLC, Reno, NV (US)

(72) Inventors: Laurent Lefort, Maastricht (NL); Mike Schmitkamp, Herzogenrath (DE)

(73) Assignee: Deuteria Beverages, LLC, Reno, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/456,319

(22) Filed: Jun. 28, 2019

(65) Prior Publication Data

US 2020/0189991 A1    Jun. 18, 2020

Related U.S. Application Data

(63) Continuation of application No. 15/964,012, filed on Apr. 26, 2018, now Pat. No. 10,343,955.

(60) Provisional application No. 62/491,181, filed on Apr. 27, 2017.

(51) Int. Cl.
| | | |
|---|---|---|
| *C07B 59/00* | (2006.01) | |
| *B01J 31/18* | (2006.01) | |
| *C07C 29/149* | (2006.01) | |
| *B01J 31/24* | (2006.01) | |
| *B01J 31/22* | (2006.01) | |
| *C07C 29/90* | (2006.01) | |

(52) U.S. Cl.
CPC ............ *C07B 59/001* (2013.01); *B01J 31/189* (2013.01); *B01J 31/1815* (2013.01); *B01J 31/2295* (2013.01); *B01J 31/2409* (2013.01); *C07C 29/149* (2013.01); *B01J 2231/641* (2013.01); *B01J 2231/643* (2013.01); *B01J 2531/0258* (2013.01); *B01J 2531/821* (2013.01); *B01J 2531/827* (2013.01); *C07B 2200/05* (2013.01); *C07B 2200/07* (2013.01); *C07C 29/90* (2013.01); *Y10S 585/941* (2013.01)

(58) Field of Classification Search
CPC .............. C07B 59/001; C07B 2200/05; Y10S 585/941; B01J 31/1815; B01J 31/189; B01J 31/2295; B01J 31/2409; B01J 2531/0258; B01J 2531/821; C07C 29/149
See application file for complete search history.

(56) References Cited

U.S. PATENT DOCUMENTS

| | | |
|---|---|---|
| 8,003,838 B2 | 8/2011 | Dupau et al. |
| 8,658,236 B2 | 2/2014 | Czarnik et al. |
| 2008/0145303 A1 | 6/2008 | Hirota et al. |
| 2008/0234488 A1 | 9/2008 | Ito et al. |
| 2011/0237814 A1 | 9/2011 | Kuriyama et al. |
| 2013/0303774 A1 | 11/2013 | Ishii et al. |
| 2014/0081019 A1 | 3/2014 | Atzrodt et al. |
| 2016/0039853 A1 | 2/2016 | Dupau et al. |

OTHER PUBLICATIONS

Zhang, J., et al., Efficient Homogeneous Catalytic Hydrogenationof Esters to Alcohols, Catalystic Hydrogenation, Angew. Chem. Int. Ed., 45, 1113-1115 (Year: 2006).*
Zhang, Lei et al., Efficient deuterium labelling of alcohols in deuterated water catalyzed by ruthenium pincer complexes, Catalysis Communications 2016, 84, 67-70.
Chatterjee Basujit et al., The ruthenium-catalyzed selective synthesis of mono-deuterated terminal alkynes, Chem. Commun. 2016, 52, 4509-12.
Chatterjee Basujit et al., Ruthenium Catalyzed Selective a- and a,b-Deuteration of Alcohols Using D2O, Or. Lett 2015, 17, 4794-97.
PCT/US18/029660 Written Opinion dated Jul. 19, 2018 (corresponding PCT application).
PCT/US18/029660 International Search Report dated Jul. 19, 2018 (corresponding PCT application).
Khaskin, Eugene et al., Simple and Efficient Catalytic Reaction for the Selective Deuteration of Alcohols, 2013, ACS Catalysis (3), 448-52.
Maegawa, T. et al., A Convenient and Effective Method for the Regioselective Deuteration of Alcohols, Adv. Syn. Catal. 2008, 350, 2215-18.

* cited by examiner

*Primary Examiner* — Yate' K Cutliff
(74) *Attorney, Agent, or Firm* — Vance Intellectual Property, PC

(57) ABSTRACT

The invention relates to a process for the preparation of a deuterated ethanol from an acetic acid, an acetate, or an amide by reaction with $D_2$ in the presence of a transition metal catalyst.

24 Claims, No Drawings

PROCESS FOR THE PREPARATION OF DEUTERATED ETHANOL FROM D2

FIELD OF THE INVENTION

The present invention relates to a process for the preparation of a deuterated ethanol from $D_2$.

BACKGROUND OF THE INVENTION

Deuterium (D or $^2H$) is a stable, non-radioactive isotope of hydrogen. Deuterium-enriched organic compounds such as a deuterated ethanol are known. U.S. Pat. No. 8,658,236 describes an alcoholic beverage of water and ethanol, wherein at least 5 mole percent of the ethanol is a deuterated ethanol. This alcoholic beverage is believed to diminish the negative side effects associated with the consumption of ethanol.

The production of a deuterated-ethanol containing alcoholic beverage requires the preparation of a deuterated ethanol in an efficient, safe, and cost-effective manner. A known process for the preparation of a deuterated alcohol (e.g., deuterated ethanol) involves an H/D exchange reaction between a non-deuterated alcohol and $D_2O$. Depending on the process, the resulting deuterated alcohol may comprise deuterium in different positions. Examples of such processes can be found in Chemistry Letters 34, No. 2 (2005), p. 192-193 "Ruthenium catalyzed deuterium labelling of α-carbon in primary alcohol and primary/secondary amine in $D_2O$"; Adv. Synth. Catal. 2008, 350, p. 2215-2218 "A method for the regioselective deuteration of alcohols"; Org. Lett. 2015, 17, p. 4794-4797 "Ruthenium Catalyzed Selective α- and α,β-Deuteration of Alcohols Using $D_2O$" and Catalysis Communications 84 (2016) p. 67-70 "Efficient deuterium labelling of alcohols in deuterated water catalyzed by ruthenium pincer complexes".

Other routes to produce a deuterated alcohol involve several consecutive reactions requiring expensive and/or hazardous material. For each of these transformations, purification and isolation of the intermediates are necessary.

In view of the above, it is desirable to be able to synthesize deuterated ethanol in an efficient, safe and cost-effective manner. It is further desirable to synthesize deuterated ethanol with deuteration substantially only at a desired position(s).

SUMMARY OF THE INVENTION

In an aspect, the present invention provides a process for the preparation of deuterated ethanol from ethanol, $D_2$, and a catalyst.

These and other aspects, which will become apparent during the following detailed, have achieved by the inventors' discovery of a new process of making deuterated ethanol.

DETAILED DESCRIPTION OF THE INVENTION

Thus, in an aspect, the present invention provides a novel process for the preparation of a deuterated ethanol of formula (I):

$$CR^1R^2R^3CR^4R^5OD \qquad (I)$$

comprising: reacting compound (II) with $D_2$ in the presence of a catalyst of formula (III):

$$ML_aX_b \qquad (III)$$

wherein:
$R^1$-$R^5$ are independently H or D, provided that the abundance of D in $R^4$ and $R^5$ is at least 70%;
compound (II) is selected from: acetic acid, an acetate, and an amide;
M is a transition metal;
L is a ligand;
X is a counterion;
a is an integer selected from 1-5; and,
b is an integer selected from 0-5.

The abundance of D in $R^4$ and $R^5$ (the $CH_2$ position) and in $R^1$, $R^2$, and $R^3$ (the $CH_3$ position) can be measured by $^1H$ NMR. The 70% abundance of D in $R^4$ and $R^5$ means that 70% of all $R^4$ and $R^5$ present are D (as opposed to the natural abundance of 0.01%).

The process of the present invention uses $D_2$ as the deuterium source which is a non-toxic gas. The amount of the catalyst (III) required for the process is very small, making the process cost effective. Also, the catalyst (III) can be easily separated from the desired product.

In another aspect, the abundance of D in $R^4$ and $R^5$ is at least 80%. Additional examples of the abundance of D in $R^4$ and $R^5$ include at least 90, 91, 92, 93, 94, 95, 96, 97, 98, 99, and 99.5%.

In another aspect, the incorporation of D occurs preferentially in $R^4$ and $R^5$ over $R^1$-$R^3$. In another aspect, the abundance of D in $R^1$-$R^3$ is at most 50%. Additional examples of the abundance of D in $R^1$-$R^3$ include at most 45, 40, 35, 30, 25, 20, 15, 10, 5, and 1%.

In another aspect, the abundance of D in $R^4$ and $R^5$ is at least 90% and the abundance of D in $R^1$-$R^3$ is at most 5%. Additional examples include (a) at least 95% and at most 1%, and (b) at least 99% and at most 1%.

The conversion of ethanol to deuterated ethanol in the present process can be determined by $^1H$ NMR. The conversion is the molar ratio of deuterated ethanol formed divided by the initial amount of starting ethanol (un-enriched ethanol). In an aspect, the conversion percentage (molar ratio×100) is at least 90%. Additional examples of the conversion percentage include at least 95%, at least 98%, and at least 99%.

As noted above, compound (II) is selected from acetic acid, an acetate, and an amide.

In another aspect, compound (II) is acetic acid, which is a compound having the formula $CH_3COOH$ (or $CH_3CO_2H$).

In another aspect, compound (II) is an acetate of formula (IIA):

$$CH_3COOR^6 \qquad (IIA)$$

wherein:
$R^6$ is selected from: a $C_1$ or $C_{3-10}$ alkyl group, a $C_{1-10}$ substituted alkyl group, a $C_{6-18}$ aromatic ring group, a $C_{6-18}$ substituted aromatic ring group, and a glycol ether group;
alternatively, $R^6$ is selected from: —$R^7$—$OCOCH_3$ and —CH—($R^8OCOCH_3$)($R^9OCOCH_3$);
$R^7$ is selected from: a $C_{1-10}$ alkylene group, a substituted $C_{1-10}$ alkylene group, a $C_{6-18}$ aromatic ring group, a $C_{6-18}$ substituted aromatic ring group, and a glycol ether group; and,
$R^8$ and $R^9$ are independently selected from: a $C_{1-10}$ alkylene group, a substituted $C_{1-10}$ alkylene group, a $C_{6-18}$ aromatic ring group, a $C_{6-18}$ substituted aromatic ring group, and a glycol ether group.

In another aspect, in the acetate represented by the formula $CH_3COOR^6$, $R^6$ has a structure such that an alcohol made from $R^6$ represented by $R^6OH$ is a primary or a secondary alcohol. In other words, $R^6$ is bonded to CH$_3$COO— by a carbon atom having at least one H (e.g., a —CH—, CH$_2$—, or —CH$_3$ moiety).

Examples of the acetate represented by the formula CH$_3$CO$_2$R$^6$ include methyl acetate, n-propyl acetate, i-propyl acetate, n-butyl acetate, i-butyl acetate, di(propylene glycol) methyl ether acetate, and phenyl acetate.

Examples of the acetate represented by the formula CH$_3$CO$_2$R$^7$OCOCH$_3$ include ethylene glycol diacetate (R$^7$ is ethylene) and propylene glycol diacetate (R$^7$ is i-propylene).

An example of the acetate represented by the formula CH$_3$CO$_2$CH(R$^8$OCOCH$_3$)(R$^9$OCOCH$_3$) is glyceryl triacetate (R$^8$ and R$^9$=CH$_2$).

In another aspect, compound (II) is an acetate selected from: methyl acetate, n-propyl acetate, i-propyl acetate, n-butyl acetate, i-butyl acetate, di(propylene glycol) methyl ether acetate, phenyl acetate, ethylene glycol diacetate, propylene glycol diacetate, and glyceryl triacetate.

In another aspect, compound (II) is an amide of formula (IIB):

CH$_3$CO—NR$^{10}$R$^{11}$ (IIB)

wherein:
R$^{10}$ and R$^{11}$ are independently selected from: H, a C$_{1-10}$ alkyl group, a C$_{1-10}$ substituted alkyl group, a C$_{6-18}$ aromatic ring group, and a C$_{6-18}$ substituted aromatic ring group;
alternatively, R$^{10}$ and R$^{11}$ are linked to each other to form a 5-6 membered ring that optionally contains a hetero atom selected from: nitrogen, oxygen, and sulfur.

Examples of amides include CH$_3$CONH-phenyl (R$^{10}$=H, R$^{11}$=phenyl), CH$_3$CONHCH$_2$CH$_3$ (R$^{10}$=H, R$^{11}$=ethyl). Examples of NR$^{10}$R$^{11}$ being a ring include morpholine and piperidine.

In another aspect, the glycol ether group of R$^6$, R$^7$, or R$^8$ is selected from a compound of formula (IIC) and (IID):

—R$^{12}$—O—R$^{13}$ (IIC)

—R$^{12}$—O—R$^{14}$—O—R$^{13}$ (IID)

wherein:
R$^{12}$ and R$^{13}$ are independently selected from: a C$_{1-10}$ alkyl group; and,
R$^{14}$ is a C$_{1-10}$ alkylene group.

In another aspect, R$^{12}$ and R$^{13}$ are independently selected from: a C$_{1-6}$ alkyl group and R$^{14}$ is a C$_{1-6}$ alkylene group.

In another aspect, R$^{12}$=CH$_3$, R$^{13}$=CH$_3$, and R$^{14}$=—CH$_2$—.

The catalyst of formula (III) is suitable for the reduction of an ester or an amide to the corresponding alcohol or amine.

In another aspect, transition metal "M" is selected from: Fe, Co, Ni, Mn, Pd, Pt, Rh, Ru, Os and Ir.

In another aspect, the transition metal is selected from: Pd, Pt, Rh, Ru and Ir.

In another aspect, the transition metal is Ru.

Ligand "L" is any ligand suitable for the reduction of esters or amides. In another aspect, the ligand is selected from: a monodentate ligand and a polydentate ligand. Examples of monodentate ligands include phosphine (e.g., triphenylphosphine), carbon monoxide, an olefin, water, acetonitrile, dimethylsulfoxide. Examples of polydentate ligands include an olefin (e.g., cyclooctadiene), an amino phosphine (e.g., 2-(diphenylphosphanyl)ethan-1-amine and bis(2-(diphenylphosphanyl)ethyl)amine), a bypiridine (e.g., 4,4'-dimethoxy-2,2'-bipyridine).

When "a" is from 2 to 5, each of the ligands may be the same or different.

In another aspect, ligand L is carbon monoxide (CO).

In another aspect, counterion "X" is selected from: pentamethylcyclopentadienyl, chloride, bromide, iodide, hydride, triflate, and BH$_4$.

When "b" is from 2 to 5, each of the counterions may be the same or different.

In another aspect, one of the counterions X is hydride.

In another aspect, M, L, and X are as follows:
M is Ru;
L is selected from phosphine, carbon monoxide, olefin, water, acetonitrile, dimethylsulfoxide, amino phosphine, and bypiridine; and,
X is selected from pentamethylcyclopentadienyl, chloride, bromide, iodide, hydride, triflate, and BH$_4$.

In another aspect, the catalyst is a ruthenium complex of general formula (IV):

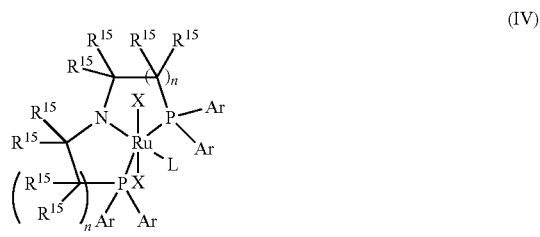

wherein:
each R$^{15}$ is independently selected from: a hydrogen atom, a C$_{1-10}$ alkyl group, a substituted C$_{1-10}$ alkyl group, a C$_{6-18}$ aromatic ring group, and a substituted C$_{6-18}$ aromatic ring group;
each Ar is independently selected from a C$_{6-18}$ aromatic ring group and a substituted C$_{6-18}$ aromatic ring group; and,
each n is independently selected from an integer of 1 or 2.

The ruthenium catalysts of formula (IV) are known (see U.S. Pat. No. 8,003,838, US2013/0303774, and US2016/0039853, which are incorporated herein by reference).

In another aspect, the ligand L is a monodentate ligand.

In another aspect, L is selected from: phosphine (e.g., triphenylphosphine), carbon monoxide, olefin, water, acetonitrile and dimethylsulfoxide.

In another aspect, L is carbon monoxide.

In another aspect, X is selected from: pentamethylcyclopentadienyl, chloride, bromide, iodide, hydride, triflate, and BH$_4$.

In another aspect, one of X is hydride.

In another aspect, in formula (IV) two vicinal R$^{15}$ (except hydrogen atoms) may form a cyclic structure by covalent bond of carbon atoms through or without a nitrogen atom, an oxygen atom or a sulfur atom.

In another aspect, in formula (IV), each Ar is phenyl.

In another aspect, n is 1 (each P is bound to the N in the Ru complex via a 2 carbon linker).

In another aspect, n is 2 (each P is bound to the N in the Ru complex via a 3 carbon linker).

In another aspect, n=1 and all R$^{12}$=hydrogen.

In another aspect, L is carbon monoxide and one of X is hydride.

In another aspect, the catalyst is a Ru complex of formula (V) (which is commercially available as Ru-MACHO®) ({Bis[2-(diphenylphosphino)ethyl]amine}carboynlchlorohydridoruthenium(II)):

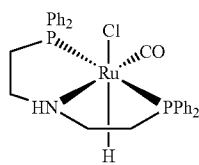

(V)

wherein Ph=phenyl.

In another aspect, the catalyst is a Ru complex of formula (VI) (which is commercially available as Ru-MACHO®-BH)(Carbonylhydrido(tetrahydroborato)[bis(2-diphenylphosphinoethyl)amino]ruthenium(II)):

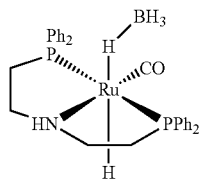

(VI)

wherein Ph=phenyl.

In another aspect, the catalyst is a Ru complex of formula (VII) (Ru-Firmenich as described in Angew. Chem. Int. Ed. 2007, 46, 7473-7476);

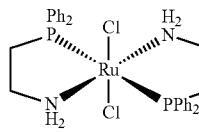

(VII)

wherein Ph=phenyl.

In another aspect, the catalyst is a Ru complex of formula (VIII) (Cp₃Ir(BiPy)(OTf)₂ as described in JACS, 2013, 135, 16022));

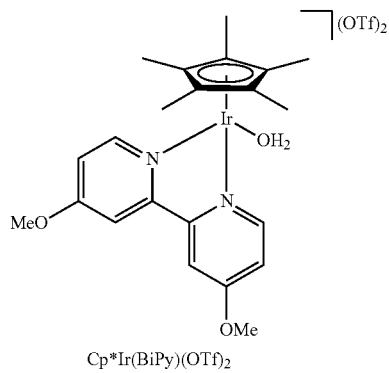

(VIII)

Cp*Ir(BiPy)(OTf)₂ wherein Cp=cyclopentadienyl, BiPy=bipyridine, and OTf=triflate.

In another aspect, the catalyst is the compound of formula (VI) and the reaction is performed in the absence of a base. This results in a high selectivity for the D incorporation in $R^4$-$R^5$ over $R^1$-$R^3$.

In another aspect, when the catalyst is the compound of formula (VI), then compound (II) is selected from: methyl acetate, n-propyl acetate, i-propyl acetate, n-butyl acetate, i-butyl acetate, and glyceryl triacetate.

In another aspect, the reaction is performed in the absence of base.

In another aspect, the reaction is performed in the presence of base.

Examples of the base include
a. alkali metal hydrogen carbonates (e.g., $LiHCO_3$, $NaHCO_3$, and $KHCO_3$); alkali metal carbonates (e.g., $Li_2CO_3$, $Na_2CO_3$, and $K_2CO_3$);
b. alkali metal hydroxides (e.g., LiOH, NaOH, and KOH);
c. tetraalkyl ammonium hydroxides (e.g., $N(CH_3)_4OH$, $N(CH_2CH_3)_4OH$, $N(CH_2CH_2CH_3)_4OH$, and $N(CH_2CH_2CH_2CH_3)_4OH$,);
d. alkali metal alkoxides (e.g, $LiOCH_3$, $NaOCH_3$, $KOCH_3$, $LiOCH_2CH_3$, $NaOCH_2CH_3$, $KOCH_2CH_3$, $LiOCH(CH_3)_2$, $NaOCH(CH_3)_2$, $KOCH(CH_3)_2$, $LiOC(CH_3)_4$, $NaOC(CH_3)_4$, $KOC(CH_3)_4$;
e. organic bases (e.g., triethylamine, diisopropylethylamine, 4-dimethylaminopyridine, and 1,8-diazabicyclo [5.4.0]undec-7-ene);
f. alkali metal bis(trialkylsilyl)amides (e.g., lithium bis(trialkylsilyl)amide, sodium bis(trialkylsilyl)amide, and potassium bis(trialkylsilyl)amide); and
g. alkali metal borohydrides (e.g., $LiBH_4$, $NaBH_4$, and $KBH_4$).

In another aspect, the reaction is performed in the presence of an alkali metal alkoxide. Examples of alkali metal alkoxides include $LiOCH_3$, $NaOCH_3$, and $KOCH_3$.

In another aspect, the reaction is performed in the presence of an alkali metal borohydride. Examples of alkali metal borohydrides include $LiBH_4$, $NaBH_4$, and $KBH_4$.

In another aspect, the amount of the base is 0.1, 0.2, 0.3, 0.4, 0.5, 0.6, 0.7, 0.8, 0.9, 1, 2, 3, 4, 5, 6, 7, 8, 9, to 10 mol % with respect to compound (II).

In another aspect, the catalyst is compound (V) (Ru-MACHO®) and the reaction is performed in the presence of a base. Examples of the base include $NaBH_4$ and $KOCH_3$. In another example, the base is $NaBH_4$. The combination of Ru-MACHO® and $NaBH_4$ results in a high selectivity for the D incorporation in $R^4$-$R^5$ over $R^1$-$R^3$.

In another aspect, the catalyst is compound (VI) (Ru-MACHO®-BH) and the reaction is performed in the presence of a base.

In another aspect, the catalyst is compound (VI) (Ru-MACHO®-BH) and the reaction is performed in the absence of a base. This results in a high selectivity for the D incorporation in $R^4$-$R^5$ over $R^1$-$R^3$.

In another aspect, the catalyst is compound (VII) (Ru-Firmenich) and the reaction is performed in the presence of a base. Examples of the base include $KOCH_3$ and $NaBH_4$. The use of $KOCH_3$ results in a higher conversion but low selectivity. The use of $NaBH_4$ results in a lower conversion but high selectivity.

In another aspect, the catalyst is compound (VIII) (Cp₃Ir(BiPy)(OTf)₂) and the reaction is performed in the presence of a base In another aspect, the catalyst is compound (VIII) (Cp₃Ir(BiPy)(OTf)₂) and the reaction is performed in the absence of a base.

In another aspect, the reaction is performed under neat conditions without the use of a solvent.

In another aspect, the reaction is performed in the presence of an organic solvent.

Examples of the organic solvent include:
a. aliphatic hydrocarbon solvents (e.g., n-hexane and n-heptane);
b. aromatic hydrocarbon solvents (e.g., toluene and xylene);
c. halogenated solvents (e.g., methylene chloride and 1,2-dichloroethane);
d. ether solvents (e.g., diethyl ether, 1,2-dimethoxyethane, 1,4-dioxane, tetrahydrofuran, 2-methyltetrahydrofuran, tert-butyl methyl ether, diisopropyl ether, diethylene glycol dimethyl ether, and anisole);
e. alcohol solvents (e.g., methanol, ethanol, n-propanol, isopropanol, n-butanol, tert-butanol, n-pentanol, n-hexanol, and cyclohexanol);
f. amide solvents (e.g., N,N-dimethylformamide and 1,3-dimethyl-2-imidazolidinone);
g. nitrile solvents (e.g., acetonitrile and propionitrile); and
h. dimethyl sulfoxide.

The organic solvents can be used solely or in combination of two or more thereof.

In another aspect, the solvent is selected from: tetrahydrofuran, methanol, and 1,4-dioxane.

The organic solvent may also be a deuterated organic solvent, i.e. an organic solvent listed above wherein at least one H is replaced by D. Examples include $CD_3OD$ (perdeutero-methanol) and $d_8$-tetrahydrofuran ($d_8$-THF)(perdeutero-THF).

In another aspect, the amount of solvent is 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, to 10 L per mole of compound (II).

In another aspect, the reaction is performed with a $D_2$ pressure of 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, to 20 MPa. Examples of the pressure include from 1, 2, 3, 4 to 5MPa of $D_2$.

In another aspect, the reaction temperature is at most 200° C. Examples of the reaction temperature include from 25, 30, 35, 40, 45, 50, 55, 60, 65, 70, 75, 80, 85, 90, 95, 100, 105, 110, 115, 120, to 125° C. Further examples include from 25, 30, 35, 40, 45, 50, 55, 60, 65, 70, 75, 80, 85, 90, 95 to 100° C. Other examples include from 70, 71, 72, 73, 74, 75, 76, 77, 78, 79, 80, 81, 82, 83, 84, 85, 86, 87, 88, 89, to 90° C. (e.g., 70-90° C.).

In another aspect, the reaction is performed at a period of 0.5, 1, 5, 10, 15, 20, 25, 30, 35, 40, 45, 50, 55, 60, 65, 70, 75, 80, 85, 90, 95 to 100 hours. Examples of the time the reaction is performed include from 1, 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70 to 72 hours.

In another aspect, compound (I) can be separated from the reaction product by any ordinary post treatment operation for organic synthesis. Further, the crude product can be purified to a high purity, as needed, by standard methods including, activated carbon treatment, fractional distillation, recrystallization, and column chromatography. It can be convenient to directly subject the completed reaction solution to a distillation recovery operation.

In the case where the reaction is performed in the presence of a base, the target compound of relatively high acidity tends to form a salt or complex with the base used and remain in the distillation residue during distillation recovery operation. In such a case, the target compound can be obtained with high yield by neutralizing the reaction completed solution with an organic acid (e.g., formic acid, acetic acid, citric acid, oxalic acid, benzoic acid, methanesulfonic acid or paratoluenesulfonic acid) or an inorganic acid (e.g., HCl, HBr, $HNO_3$, $H_2SO_4$) in advance, and then, subjecting the neutralized reaction completed solution to a distillation recovery operation (including recovery by washing the distillation residue with an organic solvent such as diisopropyl ether).

It is noted that the invention relates to all possible combinations of features described herein. It will therefore be appreciated that all combinations of features relating to the composition according to the invention; all combinations of features relating to the process according to the invention and all combinations of features relating to the composition according to the invention and features relating to the process according to the invention are described herein.

It should be understood that a description on a product/composition comprising certain components also discloses a product/composition consisting of these components. The product/composition consisting of these components may be advantageous in that it offers a simpler, more economical process for the preparation of the product/composition. Similarly, it should be understood that a description on a process comprising certain steps also discloses a process consisting of these steps. The process consisting of these steps may be advantageous in that it offers a simpler, more economical process.

Definitions

The examples provided in the definitions present in this application are non-inclusive unless otherwise stated. They include but are not limited to the recited examples.

When values are mentioned for a lower limit and an upper limit for a parameter, ranges made by the combinations of the values of the lower limit and the values of the upper limit are also understood to be disclosed.

"Alkyl" includes the specified number of carbon atoms in a linear, branched, and cyclic (when the alkyl group has 3 or more carbons) configuration. Alkyl includes a lower alkyl groups ($C_1$, $C_2$, $C_3$, $C_4$, $C_5$, and $C_6$ or 1-6 carbon atoms). Alkyl also includes higher alkyl groups (>$C_6$ or 7 or more carbon atoms).

When an "ene" terminates a group it indicates the group is attached to two other groups. For example, methylene refers to a —$CH_2$-moiety.

"Alkenyl" includes the specified number of hydrocarbon atoms in either straight or branched configuration with one or more unsaturated carbon-carbon bonds that may occur in any stable point along the chain, such as ethenyl and propenyl. $C_{2-6}$ alkenyl includes $C_2$, $C_3$, $C_4$, $C_5$, and $C_6$ alkenyl groups.

"Alkynyl" includes the specified number of hydrocarbon atoms in either straight or branched configuration with one or more triple carbon-carbon bonds that may occur in any stable point along the chain, such as ethynyl and propynyl. $C_{2-6}$ alkynyl includes $C_2$, $C_3$, $C_4$, $C_5$, and $C_6$ alkynyl groups.

"Substituted alkyl" is an alkyl group where one or more of the hydrogen atoms have been replaced with another chemical group (a substituent). Substituents include: halo, OH, OR (where R is a lower alkyl group), $CF_3$, $OCF_3$, $NH_2$, NHR (where R is a lower alkyl group), $NR^xR^y$ (where $R^x$ and $R^y$ are independently lower alkyl groups), $CO_2H$, $CO_2R$ (where R is a lower alkyl group), $C(O)NH_2$, $C(O)NHR$ (where R is a lower alkyl group), $C(O)NR^xR^y$ (where $R^x$ and $R^y$ are independently lower alkyl groups), CN, $C_{2-6}$ alkenyl, $C_{2-6}$ alkynyl, $C_{6-12}$ aromatic ring group, substituted $C_{6-12}$ aromatic ring group, 5-12 membered aromatic heterocyclic group, and substituted 5-12 membered aromatic heterocyclic group.

Examples of the aromatic ring group are aromatic hydrocarbon groups as typified by phenyl, naphthyl and anthryl.

Examples of the aromatic heterocyclic group are aromatic hydrocarbon groups containing hetero atoms e.g. as nitrogen, oxygen or sulfur as typified by pyrrolyl (including nitrogen-protected form), pyridyl, furyl, thienyl, indolyl (including nitrogen-protected form), quinolyl, benzofuryl and benzothienyl.

"Substituted aromatic ring group" or "substituted aromatic heterocyclic ring group" refers to an aromatic/aromatic heterocyclic ring group where at least one of the hydrogen atoms has been replaced with another chemical group. Examples of such other chemical groups include: halo, OH, $OCH_3$, $CF_3$, $OCF_3$, $NH_2$, NHR (where R is a lower alkyl group), $NR^xR^y$ (where $R^x$ and $R^y$ are independently lower alkyl groups), $CO_2H$, $CO_2R$ (where R is a lower alkyl group), $C(O)NH_2$, C(O)NHR (where R is a lower alkyl group), $C(O)NR^xR^y$ (where $R^x$ and $R^y$ are independently lower alkyl groups), CN, lower alkyl, aryl, and heteroaryl.

"Halo" refers to Cl, F, Br, or I.

Other features of the invention will become apparent in the course of the following descriptions of exemplary embodiments that are given for illustration of the invention and are not intended to be limiting thereof.

EXAMPLES

The structures of the compound (II) tested are as follows:

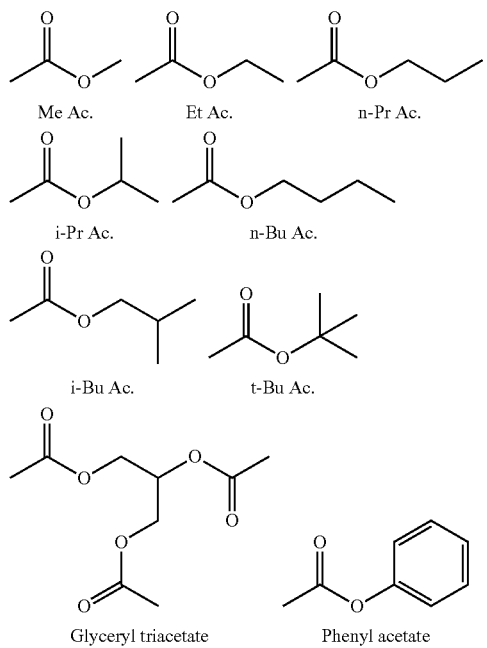

The structures of the catalysts used are shown below.

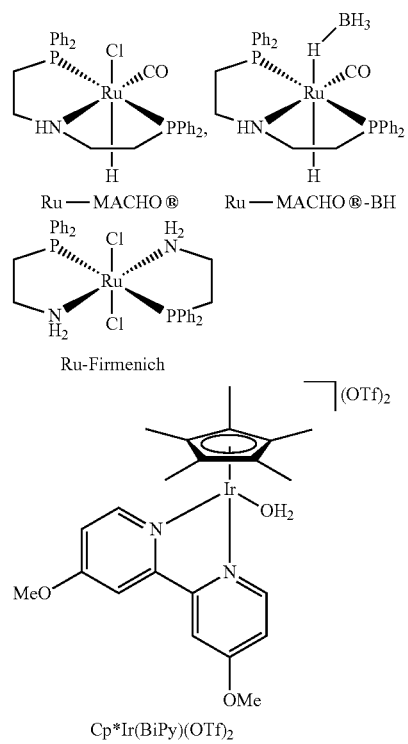

Experiment Set 1

In a glovebox, under Na atmosphere, the catalyst (and base when required) was placed inside 5 mL vials under $N_2$ atmosphere. The solvent when used was added followed by the substrate (compound (II)). The vial was placed inside an autoclave and purged with $D_2$. The pressure of $D_2$ was increased to 50 bar and the temperature was increased to 70° C. while stirring at 500 rpm with a magnetic stirred. After 16 h, the reaction mixture was cooled. After purging with $N_2$, the autoclave was opened and the reaction mixture was analyzed by $^1H$ NMR to determine the conversion and D incorporation.

The reaction conditions were as follows: 50 bar $D_2$, Substrate=15-20 wt %, ratio of Substrate/Catalyst=1000, Base=5 mol % relative to substrate when present, 70° C., 16 h.

The experiments were performed using methyl acetate with various catalysts. Results are shown in Table 1.

TABLE 1

| Exp | Catalyst Id | mmol | Substrate | Solvent | Conv (%) | D inc. at $CH_2$ (%) | D inc. at $CH_3$ (%) |
|---|---|---|---|---|---|---|---|
| 1 | Ru-MACHO-BH | 0.027 | Me Acetate | neat | >99 | >99 | <1 |
| 2 | Ru-MACHO-BH | 0.0027 | Me Acetate | $d_8$-THF (1.4 mL) | >99 | >99.2 | <1 |
| 3 | Ru-MACHO-BH | 0.0027 | Me Acetate | $d_4$-MeOH (1.4 mL) | >99 | 99 | 3 |
| 4 | Ru-MACHO | 0.0027 | Me Acetate | $d_8$-THF (1.7 mL) | >99 | 95 | 68 |
| 5 | Ru-Firmenich | 0.0027 | Me Acetate | $d_8$-THF (1.7 mL) | >99 | 90 | 92 |

For experiments 4 and 5, KOMe (potassium methoxide) was added (50 eq/Ru).

The reaction of the acetate with $D_2$ results in a deuterated ethanol and a further (side-product) alcohol. The type of the further alcohol depends on the type of the acetate, e.g. when the acetate is methyl acetate, the further alcohol is methanol. The abundance of D in the $CH_2$ position and the $CH_3$ position was determined by subjecting the resulting mixture to $^1H$ NMR. The abundance of D in the $CH_2$ position was determined by the amount of the residual H in the $CH_2$ position. The "residual H at the $CH_2$ position" was determined by the normalized ratio of area of the $CH_2$ signal in the ethanol produced divided by the area of the signal of the further alcohol. The complement to 100 of this quantity equals to the abundance of D in the $CH_2$ position. The abundance of D in the $CH_3$ position was determined in a similar manner.

In Exp 1, Ru-MACHO-BH gives full conversion of methyl acetate to a deuterated ethanol with a deuterium incorporation over 99% in the $CH_2$ position and no significant deuterium incorporation in the $CH_3$ position. The reaction was conducted without any solvent. Similar results were obtained when the reaction is done in THF or MeOH as solvent (Exp 2 and 3).

Ru-MACHO (Exp 4) or Ru-Firmenich (Exp 5) need to be activated by a strong base such as KOMe. In this case, a good conversion of Me acetate was observed but a significant D incorporation at $CH_3$ was also observed.

Exp 1 was repeated except that the pressure was 5 bar $D_2$ instead of 50 bar $D_2$. The conversion was 87% with 99% D incorporation at $CH_2$ position.

Experiment Set 2

The experiments were performed in the same way as in Experiment Set 1 using various substrates with Ru-MACHO-BH, except experiment 11 which uses Ru-MACHO. Results are shown in Table 2.

TABLE 2

| Exp | Id | mmol | Substrate | Solvent | Conv (%) | D inc. at $CH_2$ (%) | D inc. at $CH_3$ (%) |
|---|---|---|---|---|---|---|---|
| 6 | Ru-Macho-BH | 0.027 | n-Pr Acetate | neat | >99 | 77 | low if any |
| 7 | Ru-Macho-BH | 0.027 | n-Bu Acetate | neat | >99 | 77 | low if any |
| 8 | Ru-Macho-BH | 0.027 | i-Pr Acetate | neat | 75 | 92 | low if any |
| 9 | Ru-Macho-BH | 0.027 | i-Bu Acetate | neat | 100 | 77 | low if any |
| 10 | Ru-Macho-BH | 0.011 | Glyceryl triacetate | neat | 67 | 99 | |
| 11 | Ru-Macho | 0.0017 | tBu Acetate | $d_8$-THF (1.5 mL) | 32 | n.d. | n.d. |

When Ru-Macho-BH was used as the catalyst, methyl acetate led to the highest selectivity for the D-incorporation at $CH_2$. The other acetates were also tested with Ru-Macho-BH without any solvent (Exp 6-10). Good conversions were obtained in all cases. However, a lower D incorporation at $CH_2$ position was obtained by the other acetates compared with methyl acetate (Exp 1). This may be due to H/D exchange between the alcohols formed. This H/D exchange may not occur in the case of MeOH produced when the acetate is methyl acetate.

Further, deuterated ethanol was obtained from tBu acetate using Ru-Macho as the catalyst although at a lower conversion (Ex 11).

Experiment Set 3

The experiments were performed in the same way as in Experiment set 1 using methyl acetate with various catalysts. Results are shown in Table 3.

The reaction conditions were as follows: neat, $P(D_2)=50$ bar, $T=90°$ C., time=16 h.

TABLE 3

| Exp | Catalyst | mmol Cat | Subs. | Mmol | tot V (mL) | S:Cat | Conv (%) | D inc. at $CH_2$ (%) | D inc. at $CH_3$ (%) |
|---|---|---|---|---|---|---|---|---|---|
| 12 | Ru-Macho-BH | 0.011 | Me Acetate | 13.8 | 1.1 | 1285 | >99 | 97 | low if any |
| 13 | Ru-Macho + $NaBH_4$ (15 eq/Ru) | 0.0155 | Me Acetate | 6.3 | 0.5 | 406 | >99 | 87 | low if any |
| 14 | Ru-Firmenich + $NaBH_4$ (7 eq/Ru) | 0.007 | Me Acetate | 6.3 | 0.5 | 900 | 36 | >99 | 20 |
| 15 | Cp*Ir(BiPy)(OTf)$_2$ | 0.023 | Me Acetate | 6.3 | 0.5 | 274 | 41 | >99 | 22 |

In Exp 13, the in-situ activation of Ru-Macho with NaBH$_4$ also gives an active catalyst leading to a good D incorporation. The selectivity towards D incorporation at the CH$_2$ position is higher than when KOMe is used as the base. The Firmenich catalyst activated in-situ with NaBH$_4$ led to an excellent D incorporation at CH$_2$ position but also with some D incorporation at CH$_3$ position. The conversion is lower than when KOMe is used as the base. In Exp 15, a catalyst based on Ir instead of Ru was also successful at producing the desired deuterated ethanol.

Numerous modifications and variations of the present invention are possible in light of the above teachings. It is therefore to be understood that within the scope of the appended claims, the invention may be practiced otherwise that as specifically described herein.

What is claimed is:

1. A process for the preparation of a deuterated ethanol of the formula (I)

$$CR^1R^2R^3CR^4R^5OD \quad (I)$$

comprising: reacting compound (II) with D$_2$ in the presence of a catalyst of formula (IV):

(IV)

[structure of catalyst with R$^{15}$ groups, N, Ru, P, Ar, X, L]

wherein:
R$^1$-R$^5$ are independently H or D, provided that the abundance of D in R$^4$ and R$^5$ is at least 80% and the abundance of D in R$^1$-R$^3$ is at most 50%;
each R$^{15}$ is independently selected from: a hydrogen atom, a C$_{1-10}$ alkyl group, a substituted C$_{1-10}$ alkyl group, a C$_{6-18}$ aromatic ring group, and a substituted C$_{6-18}$ aromatic ring group;
each Ar is independently selected from a C$_{6-18}$ aromatic ring group and a substituted C$_{6-18}$ aromatic ring group;
each n is independently selected from an integer of 1 or 2;
compound (II) is an acetate;
L is a ligand; and,
X is a counterion.

2. The process of claim 1, wherein the process has a conversion to compound (I) of at least 90%.

3. The process of claim 1, wherein compound (II) is an acetate selected from: methyl acetate, n-propyl acetate, i-propyl acetate, n-butyl acetate, i-butyl acetate, di(propylene glycol) methyl ether acetate, phenyl acetate, ethylene glycol diacetate, propylene glycol diacetate, and glyceryl triacetate.

4. The process of claim 1, wherein compound (II) is an acetate represented by the formula CH$_3$COOR$^6$, wherein an alcohol made from R$^6$ represented by R$^6$OH is a primary or a secondary alcohol.

5. The process of claim 1, wherein compound (II) is methyl acetate.

6. The process of claim 1, wherein the catalyst is selected from catalysts of formula (V) and (VI):

(V)

[structure with Ph$_2$P, Cl, Ru, CO, HN, PPh$_2$, H]

(VI)

[structure with BH$_3$, PPh$_2$, H, Ru, CO, N, PPh$_2$, H]

7. The process of claim 6, wherein the catalyst is of formula (V).

8. The process of claim 7, wherein compound (II) is selected from: methyl acetate, n-propyl acetate, i-propyl acetate, n-butyl acetate, i-butyl acetate, and glyceryl triacetate.

9. The process of claim 7, wherein compound (II) is methyl acetate.

10. The process of claim 7, wherein the reaction is performed in the presence of a base.

11. The process of claim 10, wherein the base is NaBH$_4$.

12. The process of claim 11, wherein compound (II) is selected from: methyl acetate, n-propyl acetate, i-propyl acetate, n-butyl acetate, i-butyl acetate, and glyceryl triacetate.

13. The process of claim 11, wherein compound (II) is methyl acetate.

14. The process of claim 6, wherein the catalyst is of formula (VI).

15. The process of claim 14, wherein compound (II) is selected from: methyl acetate, n-propyl acetate, i-propyl acetate, n-butyl acetate, i-butyl acetate, and glyceryl triacetate.

16. The process of claim 14, wherein compound (II) is methyl acetate.

17. The process of claim 1, wherein the reaction is performed under neat conditions without the use of a solvent.

18. The process of claim 1, wherein the reaction is performed in the presence of a solvent selected from THF, methanol, d$_8$-THF, and d$_4$-methanol.

19. The process of claim 1, wherein the reaction is performed with a D$_2$ pressure of 0.1 to 20 MPa and a temperature of 25 to 125° C.

20. The process of claim 1, wherein the reaction is performed at a temperature of 70 to 90° C.

21. The process of claim 1, wherein the abundance of D in R$^4$ and R$^5$ is at least 90%.

22. The process of claim 1, wherein the abundance of D in R$^4$ and R$^5$ is at least 90% and the abundance of D in R$^1$-R$^3$ is at most 5%.

23. The process of claim 1, wherein the abundance of D in R$^4$ and R$^5$ is at least 95% and the abundance of D in R$^1$-R$^3$ is at most 1%.

24. The process of claim 1, wherein the abundance of D in R$^4$ and R$^5$ is at least 99% and the abundance of D in R$^1$-R$^3$ is at most 1%.

* * * * *